US00PP27021P2

(12) United States Plant Patent
Vennik

(10) Patent No.: US PP27,021 P2
(45) Date of Patent: Aug. 2, 2016

(54) ***ZANTEDESCHIA* PLANT NAMED 'ROYAL PRINCESS'**

(50) Latin Name: *Zantedeschia aethiopica*
Varietal Denomination: Royal Princess

(71) Applicant: Jacqueline Vennik, Maarssen (NL)

(72) Inventor: Jacqueline Vennik, Maarssen (NL)

( * ) Notice: Subject to any disclaimer, the term of this patent is extended or adjusted under 35 U.S.C. 154(b) by 0 days.

(21) Appl. No.: 14/544,481

(22) Filed: Jan. 12, 2015

(51) Int. Cl.
*A01H 5/02* (2006.01)

(52) U.S. Cl.
USPC ..... Plt./490

(58) Field of Classification Search
USPC ..... Plt./263.1, 490
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Zantedeschia* plant named 'Royal Princess', that is characterized by its flowers that are deep rose pink in color, its high flower yield, its flowers with a long vase life, and its high tolerance to *Erwinia caratovora.*

2 Drawing Sheets

Botanical classification: *Zantedeschia aethiopica.*
Cultivar designation: 'Royal Princess'.

BACKGROUND OF THE INVENTION

The present invention relates to a new and distinct cultivar of *Zantedeschia aethiopica* and is hereinafter referred to by the cultivar name 'Royal Princess'. 'Royal Princess' represents a new herbaceous perennial grown for use as a potted plant and cut flower.

The new cultivar was derived from a controlled breeding program by the Inventor in Maarssen, The Netherlands. The objective of the breeding program was to develop new cultivars of *Zantedeschia* with high bulb multiplication rates and flowers with high yields, long vase lives, and unique colors. The Inventor made a cross in May of 2006 between the unpatented cultivar 'Pink Persuasion' as the female parent and an unnamed and unpatented proprietary plant in the Inventor's breeding program, seedling no. 0673, as the male parent. The Inventor selected 'Royal Princess' in August of 2008 as a single unique plant amongst the seedlings that resulted from the above cross.

Asexual propagation of the new cultivar was first accomplished under the direction of the Inventor by tuber division in 2009 in Breezand, The Netherlands. Asexual propagation by tuber division and tissue culture has determined that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Royal Princess' as a new and unique cultivar of *Zantedeschia.*

1. 'Royal Princess' exhibits flowers that are deep rose pink in color.
2. 'Royal Princess' exhibits flowers with a long vase life.
3. 'Royal Princess' exhibits high flower yield.
4. 'Royal Princess' has shown a high tolerance to root disease caused by *Erwinia caratovora.*

The female parent of 'Royal Princess', 'Pink Persuasion', differs from 'Royal Princess' in having smaller flowers that are pinker in color, a more vigorous growth habit, and leaves that are more speckled. The male parent of 'Royal Princess', seedling no. 0673, differs from 'Royal Princess' in having smaller flowers that are more cerise/red in color, a more compact plant habit, and leaves that are less speckled. 'Royal Princess' can be most closely compared to the cultivars 'Sumatra' (not patented), and 'Garnet Glow' (not patented). 'Sumatra' is similar to 'Royal Princess' in having flowers in the same color range. 'Sumatra' differs from 'Royal Princess' in having flowers that are less pointed in shape and pink-purple in color with green on the outer surface, leaves that are less speckled, and a plant habit that is more upright. 'Garnet Glow' is similar to 'Royal Princess' in having flowers in the same color range. 'Garnet Glow' differs from 'Royal Princess' in having smaller leaves that are less speckled, flowers that are purple-pink, and in having a plant habit that is less upright.

BRIEF DESCRIPTION OF THE DRAWING

The accompanying colored photograph illustrates the overall appearance and distinct characteristics of the new *Zantedeschia.*

The photograph in FIG. 1 was taken of a plant about 12 weeks in age as grown in a greenhouse in a 6-inch container in Honselersdijk, The Netherlands and provides a top view of 'Royal Princess' in bloom.

Figure 1:
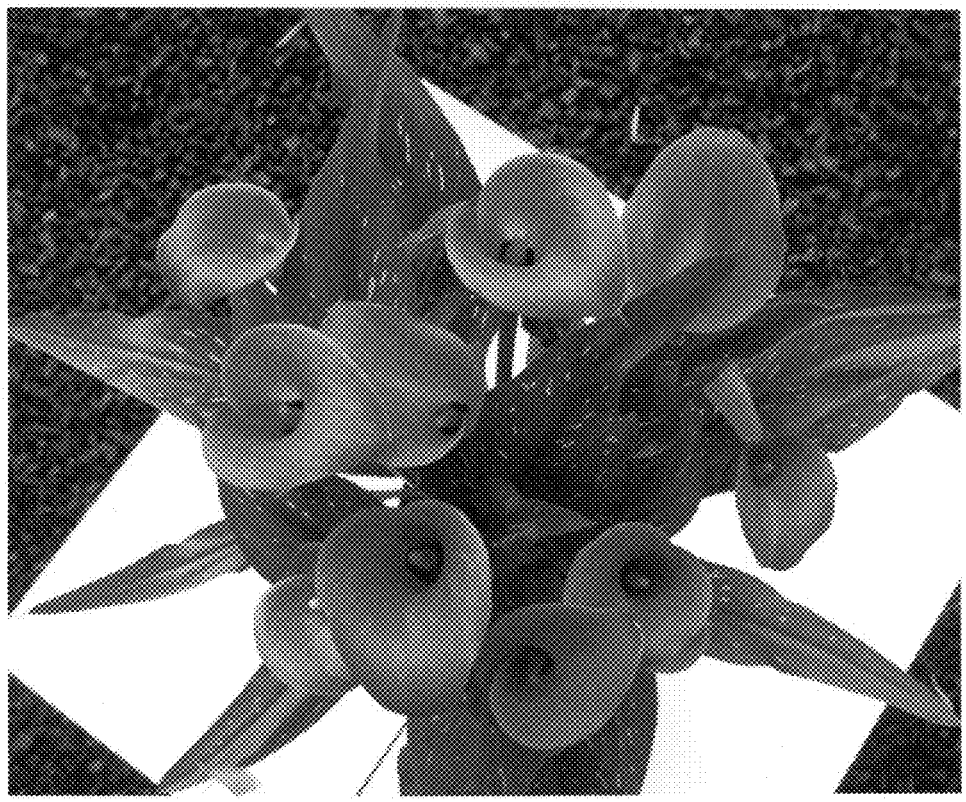
Figure 2:
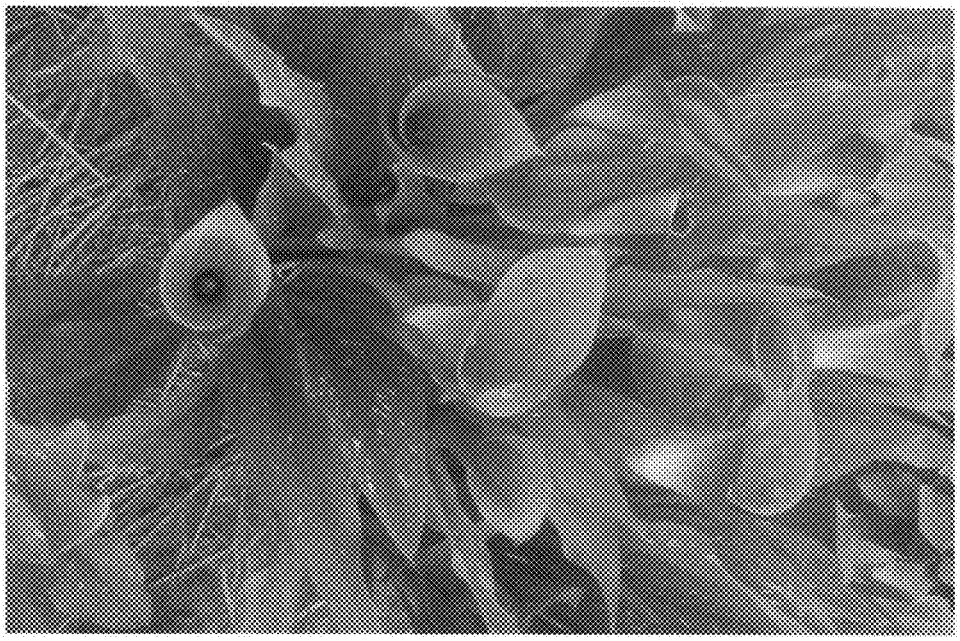

The photograph in FIG. 2 was taken of a plant about 16 weeks in age as field grown in Breezand, The Netherlands and provides a top view of 'Royal Princess' in bloom.

The colors in the photographs may differ slightly from the color values cited in the detailed botanical description, which accurately describe the colors of the new *Zantedeschia.*

DETAILED BOTANICAL DESCRIPTION OF THE PLANT

The following is a detailed description of 12 week-old plants as grown in a greenhouse in 6-inch containers in Honselersdijk, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—June in Honselersdijk, The Netherlands.

*Plant type*.—Perennial, evergreen with sufficient moisture.

*Plant habit*.—Clump forming, compact, upright with multiple stems.

*Height and spread*.—Average of 30 cm in height to top of inflorescences (25 cm to top of foliage), average of 20 cm in spread as grown in a 6-inch container (based on a 16/18 tuber size without plant growth regulators.

*Hardiness*.—Tropical plant, cold hardy at least in U.S.D.A. Zone 8, good high temperature tolerance.

*Diseases*.—Has shown high tolerance to *Erwinia caratovora*.

*Root description*.—Thick and fibrous, color about 155A.

*Branching habit*.—Clump forming plant with basal stems, no lateral branches.

*Propagation*.—Tuber division and tissue culture.

*Growth rate*.—Moderate; produces 10 to 15 harvestable shoots per year and 5 to 7 course clumps for division.

*Tuber*.—6 to 8 cm in diameter and 2 to 3 cm in length, 155A or 158D in color.

Stem description (peduncle/flowering scape):

*Shape*.—Triangular in cross-section.

*Stem color*.—A blend of 143A from the mid-section to the base and 143C at the top of the stem.

*Stem size*.—Up to 70 cm in length and 5 mm in diameter.

*Stem surface*.—Glabrous.

*Stem aspect*.—Held nearly erect, average angle 5° (straight upright=0°).

*Stem strength*.—Moderate.

*Stem number*.—An average of 8 per plant.

Foliage description:

*Leaf shape*.—Cordate to sagittate.

*Leaf division*.—Single.

*Leaf base*.—Hastate.

*Leaf apex*.—Aristate, curled downwards.

*Leaf aspect*.—Leaf is semi-erect, held at a slightly outward angle.

*Leaf venation*.—Pinnate, upper and lower surface color is N144B.

*Leaf margins*.—Entire, undulate.

*Leaf attachment*.—Petiolate.

*Leaf arrangement*.—Alternate, growing directing from base.

*Leaf surface*.—Upper and lower surface glabrous and smooth, moderately leathery, and slightly glossy, moderately covered with an average of 35 spots per leaf, spot size ranging between an average of 1 to 2 mm in width and 1 to 4 mm in length and NN155D in color.

*Leaf color*.—Young upper surface; 143A, young lower surface; 143B to 143C, mature upper surface; a blend of N137B and 147A but darker, mature lower surface; a blend of 143A and 146A.

*Leaf size*.—Up to 23.4 cm in length, widest part of leaf is up to 14 cm in width (occurs far below the middle), narrowest part of leaf is an average of 8 cm in width.

*Leaf quantity*.—Average of 4 per stem.

*Petioles*.—Average of 29.3 cm in length, 0.9 cm in width, 0.8 cm in height, and a color slightly darker than 143A.

Flower description:

*Inflorescence type*.—Spathes with spadices.

*Inflorescence size*.—Up to 8 cm in height and 6.5 cm width when fully open.

*Lastingness of inflorescence*.—An average of 3 weeks on plant and 2 weeks as a cut flower, persistent.

*Inflorescence no*.—Continuously produced from new shoots, an average of 9 open at one time as grown in a one-gallon container.

*Inflorescence bud*.—Lanceolate in shape, 7.5 cm in length and 2 cm in width, a blend of NN155C, 144D, and suffused with N77B in color, glabrous surface, opens into mature inflorescence shape which increases in size.

*Spathe*.—Ovate in shape and curled into a tube, strongly cupped with revolute margin, smooth and glabrous on all surfaces, slightly thick and leathery, arrangement; straight on top of peduncle, about 8 cm in length and 6.5 cm in width and 5 cm across, tube portion about 6 cm in length and 2.3 cm in width at mid point, apex; curled under with mucronate tip, base; broadly cuneate and wrapped around spadix, color when opening outer surface; NN155C and suffused with N77B with base 144D, color when opening inner surface; NN155C and suffused with N77B with base N77A, color when mature outer surface; a blend 144A and 138A on lower half and 59C on upper half, color when mature inner surface; 59B to 59C with very base 187A.

*Spadix*.—Cylindrical in shape tapering towards the top, placed straight on top of the peduncles, apex and base; obtuse, an average of 2.8 cm in length, upper 75% portion contains male flowers and is 5 mm in width and 13A in color, lower 25% contains female flowers and is 8 mm in width and 155A in color.

*Peduncle*.—Described under stem.

*Flower fragrance*.—None detected.

*Flower no*.—Approximately 400 male and 40 female.

*Flower type*.—Male; irregularly oblong in shape (comprised of anthers only), an average of 0.6 mm in length and 0.5 mm in width, female; globose in shape, an average of 2 mm in diameter.

Reproductive organs:

*Gynoecium*.—Ovaries 145D in color when mature, stigmas 13A in color.

*Androecium*.—Anthers 13A in color, pollen is moderate in quantity and 158A in color.

*Fruit/seed*.—No fruit or seed have been observed to date.

It is claimed:

1. A new and distinct cultivar of *Zantedeschia* plant named 'Royal Princess' as herein illustrated and described.

* * * * *